US00PP08480P

United States Patent [19]

Fussey

[11] Patent Number: Plant 8,480

[45] Date of Patent: Nov. 30, 1993

[54] DICENTRA EXIMIA 'SNOWFLAKES'

[75] Inventor: Joyce Fussey, Whitby, England

[73] Assignee: Blooms of Bressingham, Ltd., Diss, England

[21] Appl. No.: 802,002

[22] Filed: Nov. 25, 1991

[51] Int. Cl.[5] ..... A01H 5/00
[52] U.S. Cl. ..... Plt./68.1
[58] Field of Search ..... Plt./54.1, 68.1

[56] References Cited

U.S. PATENT DOCUMENTS

P.P. 1,596 4/1957 Manske ..... Plt. 68.1

*Primary Examiner*—James R. Feyrer
*Attorney, Agent, or Firm*—Keith D. Gehr

[57] ABSTRACT

A new and distinct variety of *Dicentra* eximia which bears prolific white flowers beginning in March and continuing to flower into October, although the blooming period will depend somewhat on the age of the plant and its environment. The plant is compact and ideal for use in borders or containers.

2 Drawing Sheets

The present invention relates to a new and distinct variety of a hardy perennial herbaceous plant of the genus Dicentra, a member of the Fumariaceae family.

This new variety of Dicentra was discovered as a chance seedling. It was one of about a dozen seedlings of unknown parentage grown to bulk up the stock of my small nursery in North Yorkshire, England. I was attracted to it because of the light color of its leaves which lead me to suspect that its blossoms might be white. It has been reproduced by division and from root cuttings. Each of the progeny of the first and succeeding generations exhibit characteristics identical to the mother plant. This particular variety has white blossoms and is characterized by prolific flowering, excellent vigor, and a flowering habit which extends beyond the normal flowering period for the species. Dicentra 'Snowflakes' is quite distinct from other white flowering Dicentra varieties. It forms a low spreading clump which flowers for many months, often starting as early as March and continuing until October. The finely cut foliage makes a pleasing backdrop to clusters of pendulous white flowers. The plant will thrive in habitats from full sun to partial shade where moisture is sufficient.

The flowers are of classic Dicentra type and superficially resemble those of *Dicentra formosa,* the native Pacific bleeding heart, except for color. The variety also has a resemblance to *Dicentra eximia* 'Alba' but is much more vigorous and robust.

BRIEF DESCRIPTION OF THE PHOTOGRAPHS

DETAILED PLANT DESCRIPTION

Figure 1:
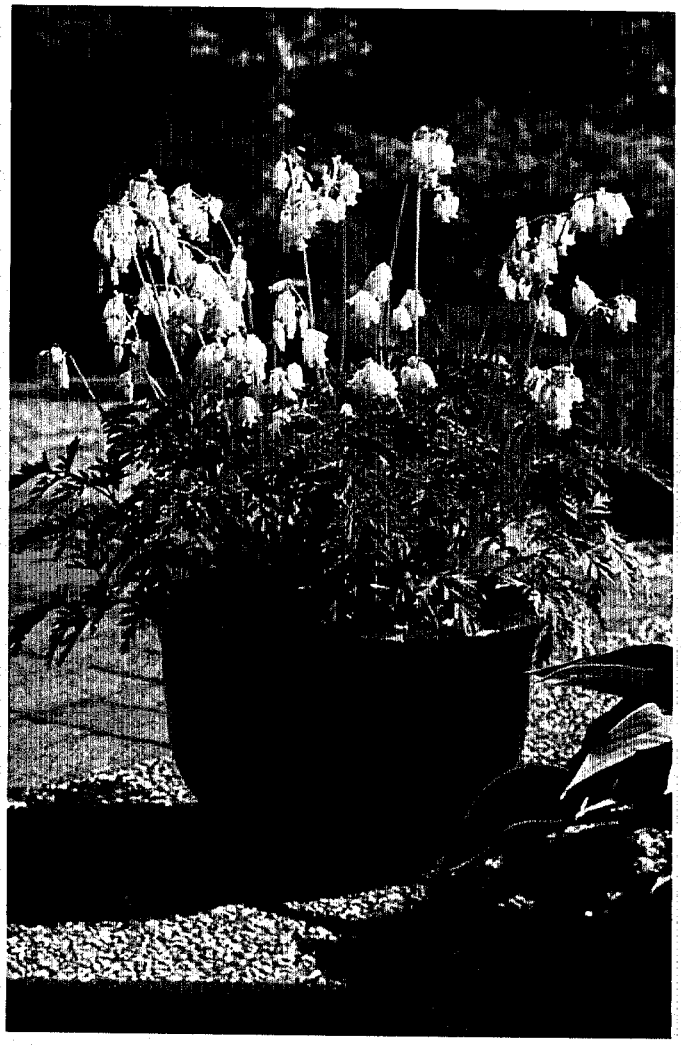
FIG. 1 is a view of Dicentra 'Snowflakes' in a container, emphasizing the finely divided foliage and the profuse blooming habit.
Figure 2:
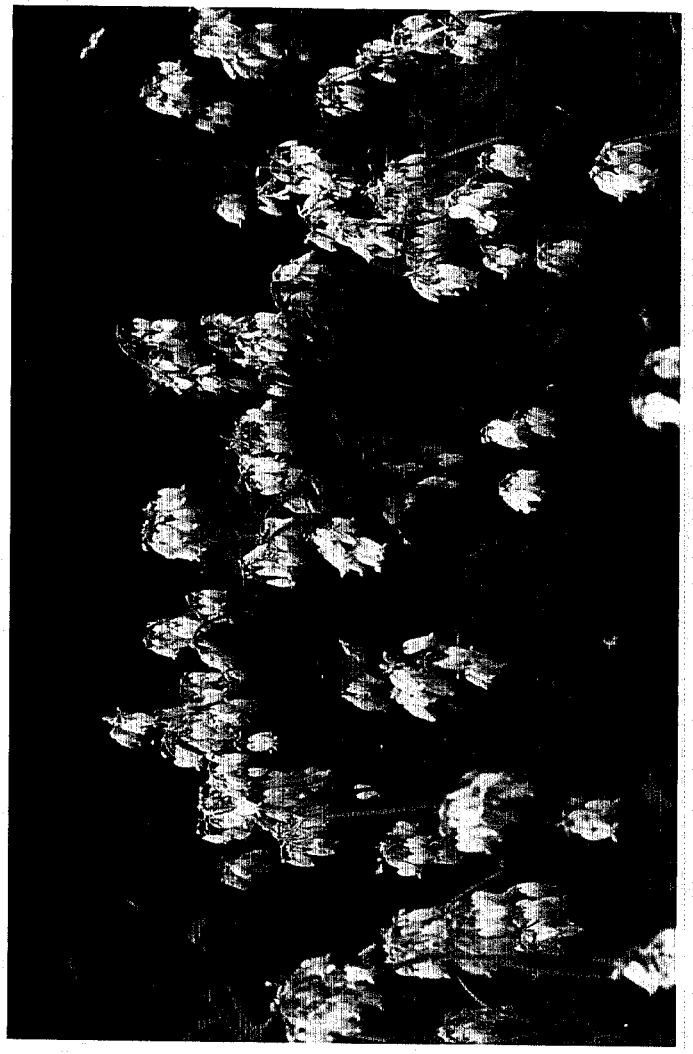
FIG. 2 is a view of the plant growing a border setting.

The following is a detailed description of the new Dicentra variety. All color determinations and comparisons are based on The Royal Horticultural Society Colour Charts.

Origin: Seedling selection.
Parentage: Unknown.

Size: Mature plants are 35–40 cm in height with a spread of about 40 cm.
Habit: Compact.
Root system: Rhizomatous.
Plant vigor: The shrub shows vigorous and healthy growth throughout Great Britain.
Blooming habit: Generally four to eight dangling white blossoms are borne on an arching raceme from a flower stem arising at the base of the plant.
Blooming period: From March continuing into October. Duration of blooming is dependent on climate and age of the plant. Younger plants will tend to have longer blooming periods than older ones. Plants growing at cool temperate sites will bloom longer than those in hotter environments. Blooming period can sometimes be extended by pinching, although this is not ordinarily necessary.
Hardiness: Winter tested throughout the British Isles. The plant has not been fully tested for maximum summer temperature tolerance.

FOLIAGE

Arrangement: Petiole arising from base of plant bearing deeply cut, fern-like bipinnate leaves.
Type: Herbaceous, dying back in winter to root stock.
Texture: Both upper and lower surfaces glabrous, lacking hairs.
Length: About 10 cm.
Width: About 12 cm.
Petiole length: 10–20 cm.
Margins: Dentate.
Apex: Entire.
Base: Cuneate.

FLOWERS

Petal count: Four, two small and two large.
Flower
*Shape.*—Cordate overall.
*Type.*—Tubular, two fused petals with small spurs.
*Size.*—About 2 cm in length.
Carpels: Very small.
Stamens: Very small.

FRUIT AND SEED

The plant does not appear to produce seed except on very rare occasions. To date only a single seed capsule has been observed. It is not known whether this seed was viable.

COLOR CHARACTERISTICS

Folaige: Mature leaves, upper surface R.H.S. Colour Chart Fan 3, Green Group 138C; lower surface Green Group 139D.

Flowers: R.H.S. Colour Chart Fan 4, White Group 155D.

I claim:

1. A new and distinct variety of *Dicentra eximia,* substantially as shown and described, characterized by prolific flowering, having clusters of white blossoms on racemes rising from the plant base, low or no seed production, excellent vigor and hardiness and a flowering season longer than normal for the species with little or no necessity for pinching to maintain blooming.

* * * * *